(12) United States Patent
Yi et al.

(10) Patent No.: US 9,724,031 B2
(45) Date of Patent: Aug. 8, 2017

(54) LANCET

(71) Applicant: Clinical Innovations, LLC, Murray, UT (US)

(72) Inventors: Patrick Yi, Walnut, CA (US); Robert L. Gibb, Jr., Whittier, CA (US)

(73) Assignee: CLINICAL INNOVATIONS, LLC, Murray, UT (US)

( * ) Notice: Subject to any disclaimer, the term of this patent is extended or adjusted under 35 U.S.C. 154(b) by 0 days.

(21) Appl. No.: 14/394,273

(22) PCT Filed: Apr. 17, 2013

(86) PCT No.: PCT/SG2013/000149
§ 371 (c)(1),
(2) Date: Oct. 14, 2014

(87) PCT Pub. No.: WO2013/158040
PCT Pub. Date: Oct. 24, 2013

(65) Prior Publication Data
US 2015/0080929 A1 Mar. 19, 2015

(30) Foreign Application Priority Data
Apr. 20, 2012 (SG) .................................. 201202916

(51) Int. Cl.
*A61B 5/15* (2006.01)
*A61B 5/151* (2006.01)

(52) U.S. Cl.
CPC .. *A61B 5/150916* (2013.01); *A61B 5/150022* (2013.01); *A61B 5/15113* (2013.01);
(Continued)

(58) Field of Classification Search
CPC ............ A61B 5/1411; A61B 5/150022; A61B 5/15113; A61B 5/15128; A61B 5/15144; A61B 5/15117; A61B 5/15019; A61B 5/150259; A61B 5/150427; A61B 5/150442; A61B 5/150465; A61B 5/150549; A61B 5/150679;
(Continued)

(56) References Cited

U.S. PATENT DOCUMENTS 4,643,189 A 2/1987 Mintz
5,196,025 A * 3/1993 Ranalletta .......... A61B 5/15186
600/583

(Continued)

OTHER PUBLICATIONS

International Search Report in priority PCT Application No. PCT/SG2013/000149.

(Continued)

*Primary Examiner* — Dianne Dornbusch
(74) *Attorney, Agent, or Firm* — TraskBritt

(57) ABSTRACT

The invention relates to a lancet for performing an incision. The lancet has a blade for providing an incision and a trigger housed in a housing. The trigger has a first trigger arm, a second trigger arm and a flexible member connected to the second trigger arm. A resilient member may be disposed within the housing in a pre-cutting state in which it stores energy and arranged to exert a force for moving the second trigger arm and the blade from a first stowed position through a cutting position and to a second stowed position.

20 Claims, 10 Drawing Sheets

(52) U.S. Cl.
CPC ...... *A61B 5/15117* (2013.01); *A61B 5/15128* (2013.01); *A61B 5/15144* (2013.01); *A61B 5/150175* (2013.01); *A61B 5/150259* (2013.01); *A61B 5/150442* (2013.01); *A61B 5/150503* (2013.01); *A61B 5/150893* (2013.01)

(58) Field of Classification Search
CPC .......... A61B 5/150916; A61B 5/15142; A61B 5/1519; A61B 5/15194; A61B 17/32093; A61B 17/3209
See application file for complete search history.

(56) References Cited

U.S. PATENT DOCUMENTS

| | | | |
|---|---|---|---|
| 5,797,940 | A * | 8/1998 | Mawhirt et al. .............. 606/167 |
| 6,042,595 | A * | 3/2000 | Morita ................. A61B 5/1411 |
| | | | 606/181 |
| 7,316,698 | B1 | 1/2008 | Galloway et al. |
| 2007/0010839 | A1* | 1/2007 | Galloway et al. ............ 606/167 |
| 2010/0010528 | A1* | 1/2010 | Shi ................................ 606/182 |
| 2010/0063418 | A1 | 3/2010 | Wessel |
| 2010/0076472 | A1 | 3/2010 | Sun |
| 2011/0264131 | A1* | 10/2011 | Sun ...................... A61B 5/1411 |
| | | | 606/182 |

OTHER PUBLICATIONS

International Preliminary Report on Patentability in priority PCT Application No. PCT/SG2013/000149.

* cited by examiner

LANCET

CROSS-REFERENCE TO RELATED APPLICATIONS

This application is a United States National Stage Application of, and claims the benefit pursuant to 35 U.S.C. §371 of International Application Serial No. PCT/SG2013/000149, filed Apr. 17, 2013, which claims priority to and the benefit of Singapore Patent Application Serial No. 201202916-1, filed Apr. 20, 2012, both of which are fully incorporated by reference herein.

FIELD OF THE INVENTION

The present invention relates generally to devices for making incisions in patients. More particularly, the present invention relates to a lancet for performing an incision.

BACKGROUND OF THE INVENTION

Devices for making incisions in patients are commonly referred to as lancets. Lancets are generally used for taking blood samples and hence are used only once and disposed. A lancet apparatus described in U.S. Pat. No. 6,042,595 has a trigger actuating element configured to disengage a spring element from the catch once a trigger arm reaches a firing position. The spring element is arranged such that when it is released, the free end of the spring element strikes or hammers and then pushes the blade through the cutting stroke.

However, a potential disadvantage of the above configuration is that the hammering action of the free end of the spring element may create an impact force on the blade which may be inconsistent with the initial force required to disengage the spring element from the catch. Therefore, as a result of the indirect force application, the incision may be inconsistent.

Further, such inconsistent incisions may cause more pain in patients, especially in infants. Further, variations in the force application due to use by different medical personnel may also result in inconsistent incisions.

Therefore, there is a need for a lancet capable of producing a consistent incision with minimal pain to the patient.

SUMMARY OF THE INVENTION

The present invention is generally related to a lancet for performing an incision.

According to an embodiment, there is a lancet comprising a blade, a trigger and a resilient member housed in a housing. The trigger comprises a first trigger arm, a second trigger arm connected to the first trigger arm through a hinge, and a flexible member connected to the second trigger arm. The flexible member may be configured to allow the blade to be manoeuvred, upon activation of the trigger, in a cutting path from a first stowed position through a cutting position to a second stowed position. In a pre-cutting state, the resilient member is disposed within the housing whereby it stores energy and is arranged to exert a force for moving the second trigger arm upon activation of the trigger.

The resilient member may be disposed between the first trigger arm and the second trigger arm.

The flexible member may be connected to an end of the second trigger arm.

The housing may comprise a first stop surface for abutting the second trigger arm with the blade in the first stowed position; and a second stop surface for abutting the second trigger arm with the blade in the second stowed position, wherein the blade is within the housing in the first stowed and second stowed positions.

The second trigger arm may be configured to slide relative to the first stop surface upon movement of the first trigger arm. For example, the second trigger arm may have a chamfered surface.

The housing may include a rear member having the first stop surface and the second stop surface, the rear member positioned to define a gap between the second stop surface and an inner wall of the housing for receiving the second trigger arm and the blade in the second stowed position.

The lancet may further comprise a blade holder connected to the flexible member for holding the blade, the blade holder being configured to allow the blade to be manoeuvred, upon activation of the trigger, in a cutting path from a first stowed position through a cutting position to a second stowed position.

The housing may include cam elements of a size and shape for guiding the blade through a path to define the cutting path. For example, the cam elements may be configured, to guide the blade through a substantially parabolic path to define a cutting path for performing the incision.

The housing may include a cam configured for guiding the blade holder and the blade toward the second stowed position.

The first trigger arm may include a base portion connected to the second trigger arm through the hinge, a second portion extending from the base portion, and a slider portion connected to the second portion, the second portion being configured, upon movement of the trigger, to allow the trigger to rotate about a pivot in the housing.

The slider portion may be configured to be slidable along surfaces in the housing.

The resilient member may be one of: a helical torsion spring, a leaf spring, a cantilever spring or a helical compression spring.

The resilient member may be a cantilever spring integral with the trigger, the cantilever spring being configured to store energy in the pre-cutting state.

The resilient member may be made of a resilient metal.

The resilient member may be made of one of: high carbon steel, stainless steel, alloy steel and nickel-base alloy.

The lancet may further comprise a trigger lock for preventing movement of the trigger.

The flexible member may have a substantially S-shaped profile.

BRIEF DESCRIPTION OF DRAWINGS

Various embodiments of the invention will now be described, by way of example only, and with reference to the accompanying drawings in which.

DETAILED DESCRIPTION

Figure 1:
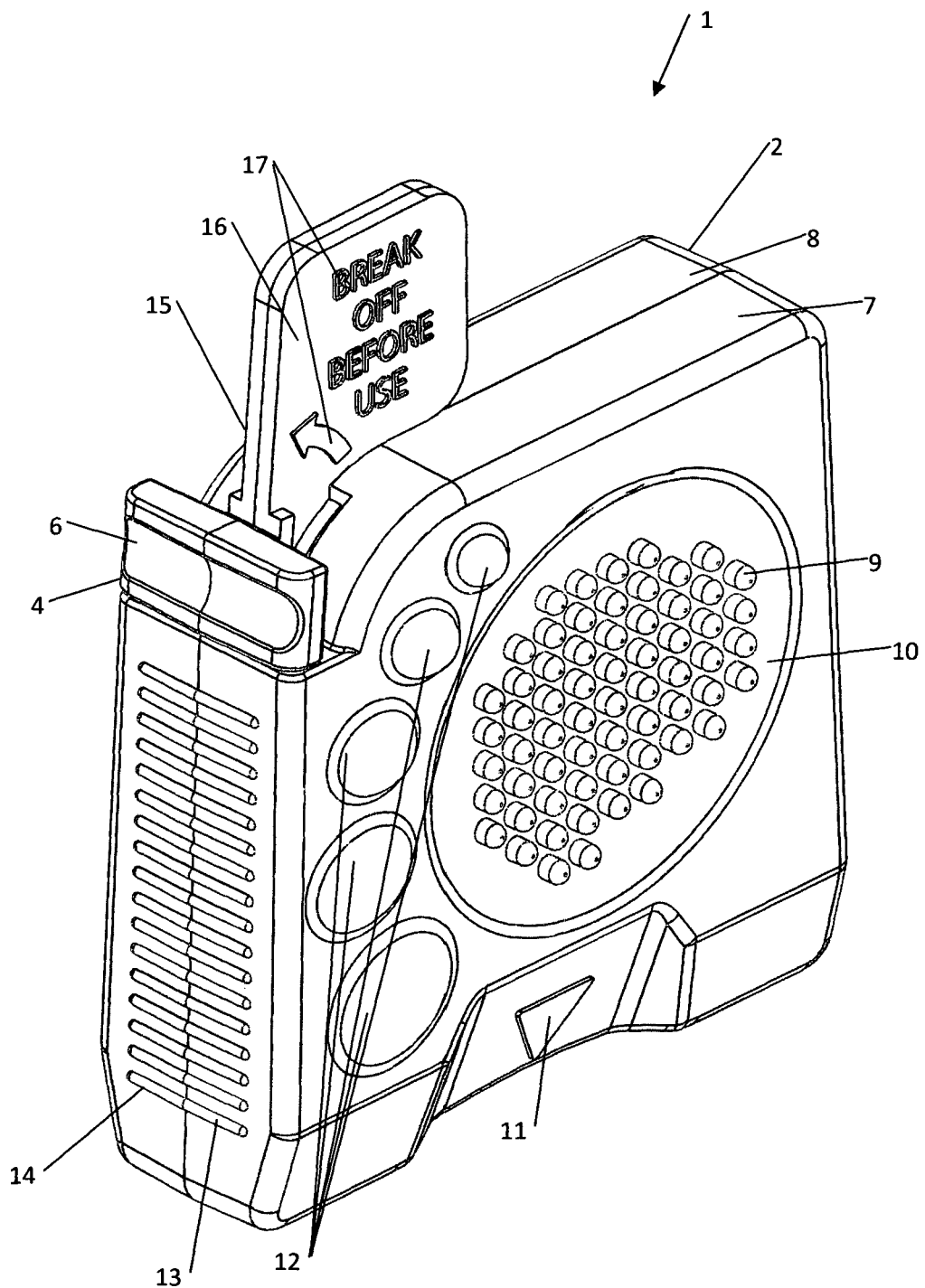
FIG. 1 is an orthogonal view of a lancet according to an embodiment.
Figure 2:
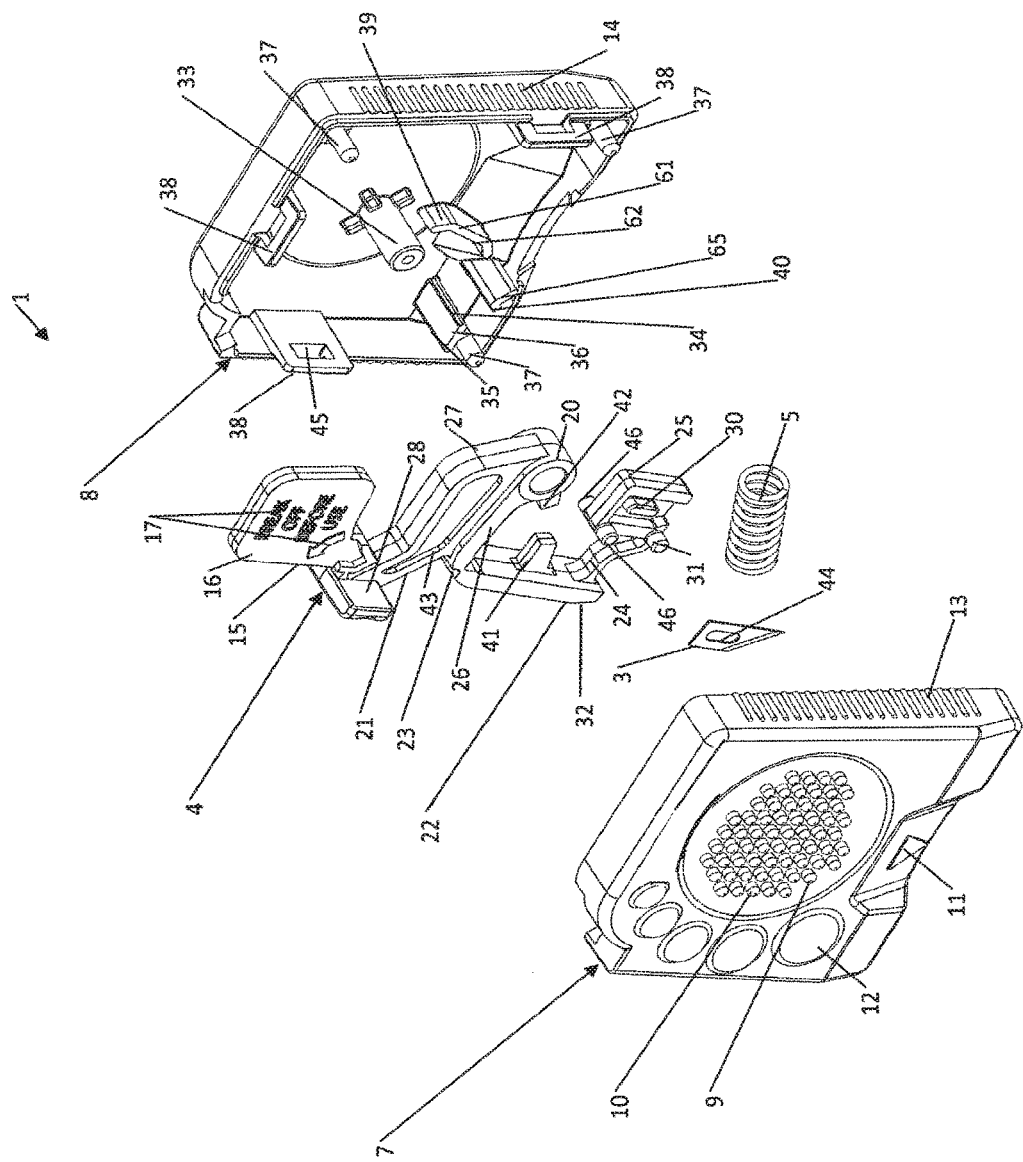
FIG. 2 is an exploded assembly view of the lancet of FIG. 1.

FIG. 1 is an orthogonal view of an embodiment of a lancet 1 for performing an incision in a region of a person in a first stowed position. FIG. 2 shows an exploded assembly of the lancet 1. Referring to FIG. 1 and FIG. 2, the lancet 1 comprises a housing 2, a blade 3 for providing an incision, a trigger 4, and a resilient member 5. The housing 2 includes a first housing part 7 and a second housing part 8 which upon assembly, form the housing 2 for housing the blade 3, the trigger 4, and the resilient member 5.

The lancet 1 may further comprise a trigger lock 15 for preventing movement of the trigger 4 and thus stopping an unintended actuation of the lancet 1. For example, the trigger lock 15 may be detachably attached to the trigger 4 and extends through an opening (not shown) of the housing 2 between the housing 2 and the trigger 4 to abut the housing 2 for preventing accidental and/or premature activation of the lancet 1. Still further, operating instructions may be located on each of two side surfaces 16 of the trigger lock 15 to guide users on the use of the lancet 1. For example, the trigger lock 15 may be a break-off tab 15 and the instructions may be in the form of raised letters 17 on the two side surfaces 16 of the break-off tab 15. The trigger 4 may have a concave recess 6 to increase grip and to give users a visual indication of where to place a finger tip for activating the lancet 1. A target incision indicator 11 may be printed on in a lower area of the housing 2 adjacent the base of the housing 2 to indicate to a user an area in the housing at which the blade 3 may extend through for performing the incision. Therefore, a user may know where to place the lancet 1 next to a target incision region. Further, the two bottom outer surfaces of the first and second housing parts 7, 8 may be substantially flat to provide a stable platform during activation of the lancet 1.

An advantage of having the concave recess 6 and the target incision indicator 11 is that the operation functions of the lancet 1 is implemented in the design of the lancet 1 to guide the user in achieving the desired result, i.e., performing an incision, in a safe and consistent manner. Hence, the process of operating the lancet 1 requires little user knowledge and hence is intuitive and user friendly. This is important for lancets because inadvertent injuries due to use of lancets can then be avoided. Still further, there may be an advantage of reduced costs in production because it may not be required to produce separate user manuals for teaching user operation of the lancet 1.

The housing parts 7 and 8 may be designed with rectilinear surfaces to increase grip when activating the lancet 1. The first and second housing parts 7, 8 may have grip features 13, 14, which upon assembly of the housing 2 form a grip patterned surface for enhancing user grip of the lancet 1. Still further, each housing part 7, 8 may include a recess 10 on an external surface to enhance grip. Alternatively, visual cues such as raised circular surfaces 12 may be provided on the housing parts 7, 8 for finger placement during use of the lancet 1. The recess 10 may have a substantially elliptical shape and a plurality of grip bumps 9 may be located in the recess 10 for enhancing grip. The housing 2 may be made of a material suitable for printing a graphic such as a logo on the housing 2. Referring to FIG. 2, the first and second housing parts 7, 8 may contain corresponding male and female alignment features for aligning and guiding the first and second housing parts 7, 8 together during assembly to form the housing 2. For example, the second housing part 8 may have three alignment post features 37 and the first housing part 7 may have three corresponding female bore features (not shown) which cooperate with the three alignment post features 37 to align and guide the first and second housing parts 7, 8 for assembly. The first and second housing parts 7, 8 may have interlocking snap features that lock the housings together to form the housing 2. For example, the second housing part 8 may have three interlocking snap features 38 located on a periphery of the second housing part 8. Each interlocking snap feature 38 has a slot 45 for receiving a corresponding snap (not shown) located on the first housing part 7. For example, the interlocking snap features may be configured for ease of assembly but designed to be difficult to disassemble due to safety reasons such as to prevent opening of the housing 2 to remove the blade 3 from the housing 2 in a post-cutting state, i.e., after the incision is performed.

The trigger 4 may be rotatably mounted relative to the housing 2 by having a hole feature 20 defined in the trigger 4 for coupling to a pivot 33 located in the second housing part 8. The trigger 4 comprises a first trigger arm 21, a second trigger arm 22 connected to the first trigger arm 21 through a hinge 23, and a flexible member 24 connected to the second trigger arm 22. The hinge 23 will be described in greater detail with reference to FIG. 4.

The flexible member 24 is configured to allow the blade 3 to be manoeuvred, upon activation of the trigger 4, in a cutting path from a first stowed position through a cutting position to a second stowed position. For example, a blade holder 25 for holding the blade 3 may be connected to the flexible member 24. The blade 3 may have a slot 44 for attaching to a locator 30 on the blade holder 25. The blade holder 25 may comprise a first plurality of cam elements 31 configured to cooperate with a cam element 39 disposed in the housing 2, for example, in the second housing part 8. The first plurality of cam elements 31 may be located on the blade holder 25 adjacent an end of the flexible member 24. The blade holder 25 may further comprise a second plurality of cam elements 46 spaced apart from the first plurality of cam elements 31. The cam element 39 may be configured for guiding the blade 3 through a cutting path by having a cam edge 61 for cooperating with the first plurality of cam elements 31 and a cam edge 62 for cooperating with the second plurality of cam elements 46. For example, the cam element 39 may be configured according to the desired cutting path such as, for example, to define a substantially parabolic cutting path for performing the incision. A cam element 40 is located in the housing 2 such as at a base of the interior of the second housing part 8 and may be configured for guiding the blade 3 toward a second stowed position in a post-cutting state whereby the blade 3 is within the housing 2. For example, the cam element 40 has a cam edge 65 for cooperating with the first plurality of cam elements 31.

The flexible member 24 may be connected to an end of the second trigger arm 22 at a distance from the hinge 23. For example, the distance may be a length of the second trigger arm 22 so as to directly transfer a force exerted by the resilient member 5 to manoeuvre the blade 3 upon activation of the trigger 4. The hinge 23 may be an integral hinge such as a molded feature pivotally connecting the first trigger arm 21 to the second trigger arm 22 for enabling the second trigger arm 22 to rotate about the hinge 23 relative to the first trigger arm 21.

The first trigger arm 21 may comprise a first trigger element 26 connected to the second trigger arm 22 via the hinge 23 so as to form a substantially "A" shape. The first trigger arm 21 may further comprise a handle portion 28 and a second trigger element 27 connecting the first trigger element 26 to the handle portion 28 wherein the concave recess 6 is provided in the handle portion 28. However, it will be appreciated that the first trigger arm 21 may also be configured such that the second trigger element 27 is connected to the second trigger arm 22 via the hinge 23 so as to form a substantially "A" shape. The second trigger element 27 may have a slot 43 defined in the second trigger element 27. The slot 43 may be configured to minimize material use in the trigger 4 and to maintain a structural integrity of the trigger 4 to prevent breakage during assembly or during activation of the lancet 1.

Figure 5:
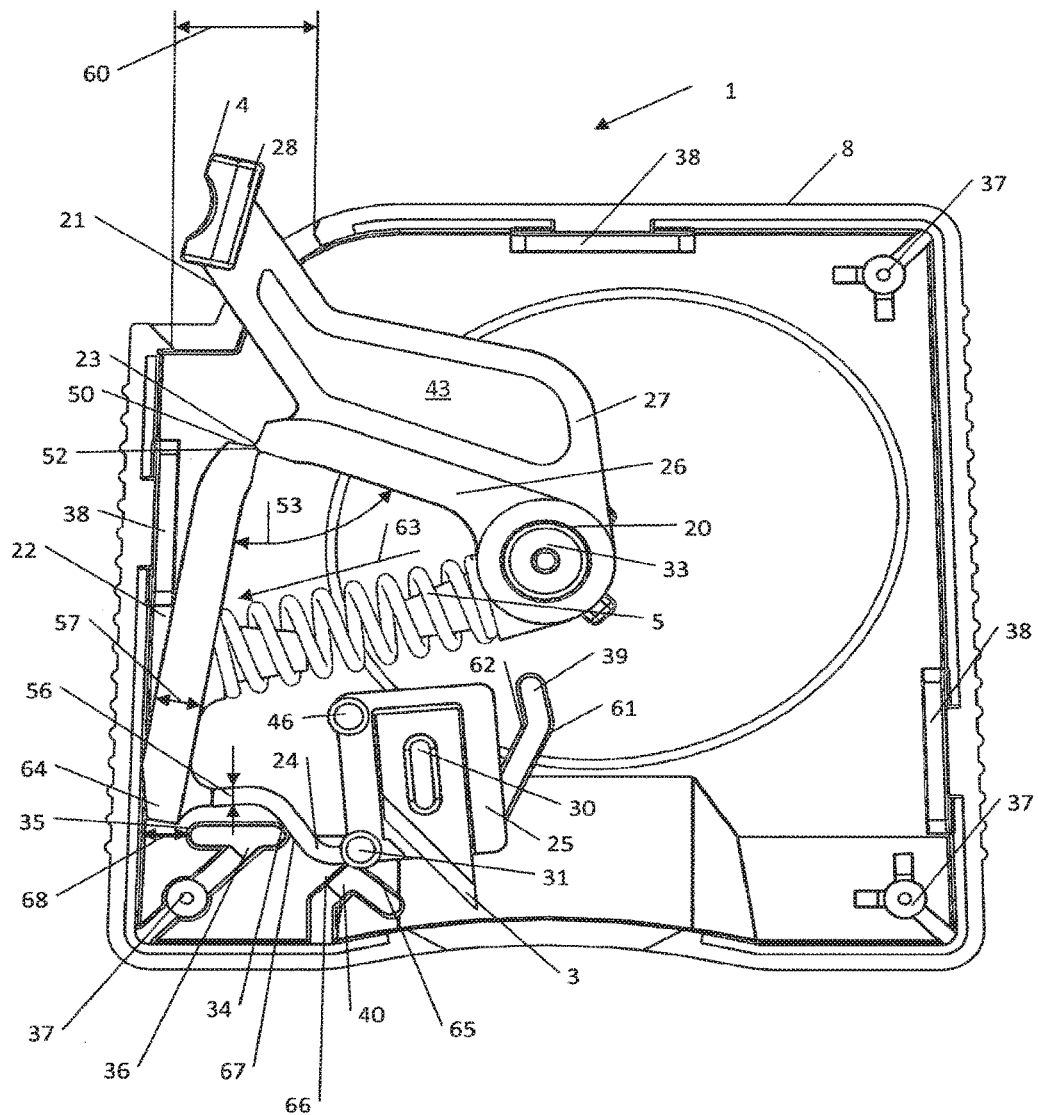
FIG. 5 is a front view of the lancet of FIG. 1 in a second stowed position.

The housing 2 may include a first stop surface 34 for abutting the second trigger arm 22 to keep the second trigger arm 22 with the blade 3 within the housing 2 in the first stowed position and a second stop surface 35 for abutting the second trigger arm 22 to keep the second trigger arm 22 with the blade 3 within the housing 2 in a second stowed position as shown in FIG. 5. For example, a rear member 36 may be provided in the second housing part 8 wherein the rear member 36 comprises the first stop surface 34 and the second stop surface 35 for abutting the second trigger arm 22 in the first and second stowed positions, respectively.

The resilient member 5 is disposed within the housing 2 in a pre-cutting state in which it stores energy and is arranged to exert a force for moving the second trigger arm 22 upon activation of the trigger 4. For example, the resilient member 5 may be supported by a locating pin 41 on the second trigger arm 22 and a locating pin 42 on the first trigger arm 21. However, it will be appreciated that the resilient member 5 may also supported by a trigger launch element (not shown) disposed in the housing instead of the locating pin 42 as long as energy may be stored in the resilient member 5 and arranged to exert a force for moving the second trigger arm 22 upon activation of the trigger 4.

The activation of the lancet 1 will be described in detail in the following description with reference to FIGS. 3, 4 and 5.

Figure 3:
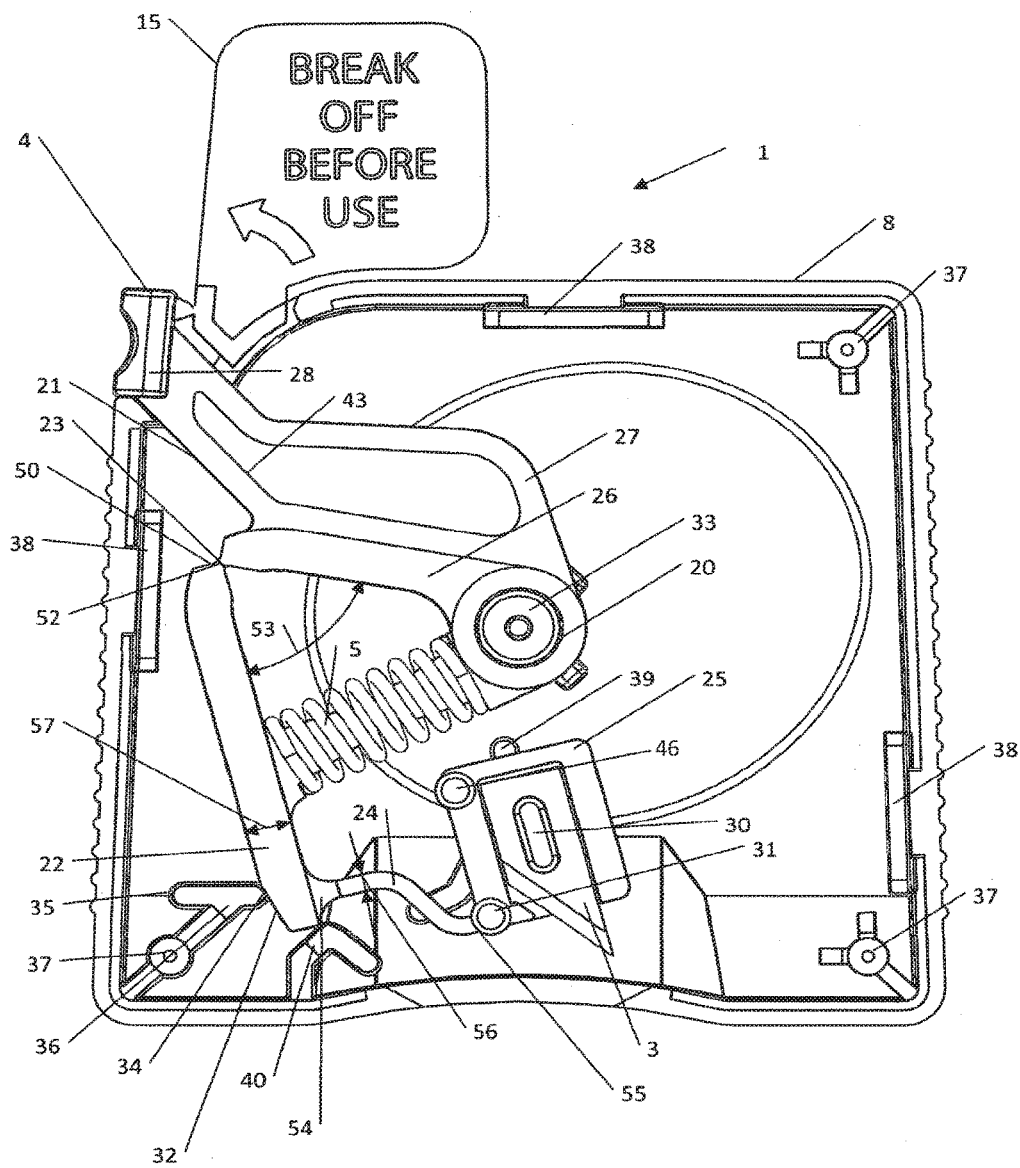
FIG. 3 is a front view of the lancet of FIG. 1 in a first stowed position.

FIG. 3 is a front view of a partial assembly of the lancet 1 in a first stowed position with the first housing part 7 removed. In the first stowed position, the resilient member 5 is disposed within the housing 2 in a pre-cutting state in which it stores energy and is arranged to exert a force for moving the second trigger arm 22 upon activation of the trigger 4. To store energy in the pre-cutting state, the resilient member 5 may be arranged between the first trigger arm 21 and the second trigger arm 22 through the locating pins 41, 42 and having one end of the resilient member 5 abutting the first stop surface 34 through the second trigger arm 22 and another end of the resilient member 5 abutting the pivot 33 through the first trigger arm 21.

The resilient member 5 may be for example a compression spring supported by the second trigger arm 22 via supports or locating pins 41, 42 (FIG. 2) on the first and second trigger arms 21, 22, respectively. The trigger 4 and the resilient member 5 may be arranged between the pivot 33 and the first stop surface 34 of the housing 2 for restraining a force generated by the resilient member 5 for moving the blade 3. The compression spring may be a helical compression spring made of metal with creep resistant properties. In the first stowed position, the second trigger arm 22 abuts the first stop surface 34 such that the resilient member 5 acts or is preloaded between the first stop surface 34 via the first and second trigger arms 21, 22 and the pivot 33 to store energy in the resilient member 5 in the first stowed position, whereby the blade 3 is within the housing 2.

Figure 4:
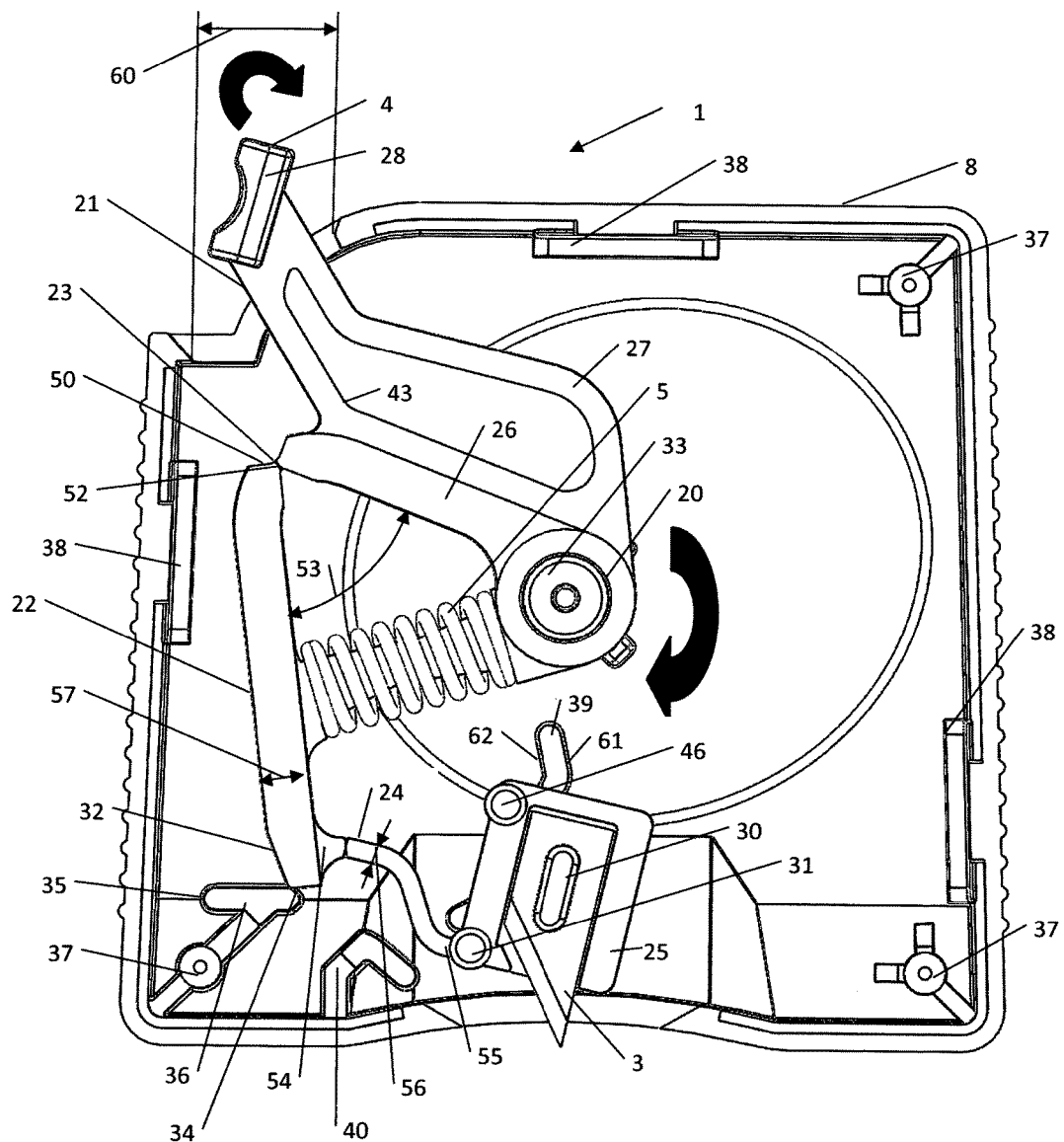
FIG. 4 is a front view of a blade of the lancet of FIG. 1 along a cutting path.

After the trigger lock 15 is removed, as shown in FIG. 4, the trigger 4 is rotatable about the pivot 33 upon a movement of the handle portion 28 through a distance 60 to activate the trigger 4. The distance 60 may correspond to a length of an opening in the housing 2 for housing the trigger lock 15. Upon activation of the trigger 4, the second trigger arm 22 may be slidable relative to the first stop surface 34 to impart the force generated by the stored energy in the resilient member 5 for moving the blade 3 or to permit release of a preloaded resilient force generated by the resilient member 5 for moving the blade 3. For example, the second trigger arm 22 may have a chamfered surface 32 for allowing the second trigger arm 22 to slide relative to the first stop surface 34. The chamfered surface 32 may be at a trigger arm tip of the second trigger arm 22 for allowing the user to activate the lancet 1 with a lower actuation force relative to a trigger arm without a chamfered profile. As the trigger arm tip of the second trigger arm 22 slides past the first stop surface 34, energy stored in the resilient member 5 in the first stowed position is transferred into a force which is exerted on the second trigger arm 22.

The second trigger arm 22 is rotatable about the hinge 23 defined by a hinge recess 50, a hinge thickness 52 and a hinge angle 53. Upon activation of the trigger 4, the hinge angle 53 increases to allow the second trigger arm 22 to move away from the first trigger arm 21 toward an inner wall of the housing 2. It will be appreciated that the hinge 23 also allows the trigger 4 and the resilient member 5 to be assembled within the housing 2 in the first stowed position.

An advantage is that the force required to manipulate the blade 3 to perform the incision is less or not dependent on a force generated by a user because the force is generated by energy stored in the resilient member 5 in the pre-cutting state. The resilient member 5 may be made of metal having creep resistant properties or designed to be creep resistant. The trigger 4 including the first and second trigger arms 21, 22, the flexible member 24 and the blade holder 25 may be an integral member made of a resilient material such as, for example, plastic.

Movement of the blade 3 in the cutting path is controlled by the flexible member 24. The flexible member 24 has a thickness 56 and a substantially S-shaped profile having a first end 54 connected to the second trigger arm 22 and a second end 55 connected to the blade holder 25. The thickness 56 of the flexible member 24 is smaller relative to a thickness 57 of the second trigger arm 22. Hence, it will be appreciated that the flexible member 24 has a greater flexibility relative to the second trigger arm 22 so as to enable the blade 3 to be manoeuvred through the blade holder 25 in a cutting path through a cutting position, as shown in FIG. 4, to a second stowed position shown in FIG. 5.

Referring to FIG. 4, upon the movement of the second trigger arm 22, the flexible member 24 flexes or deforms with the movement of the trigger arm 22 while maintaining the cam elements 31, 46 of the blade holder 25 in engagement with the cam element 39 of the housing 2. Specifically, the cam elements 31 of the blade holder 25 holding the blade 3 cooperates with a cam edge 61 of the cam element 39 to guide the blade 3 along the cutting path in a direction toward a base of the housing 2 to extend through an elongate slot (not shown) at the base of the housing 2 for performing the incision. The elongate slot may be formed upon assembly of the housing parts 7, 8 whereby each housing part 7, 8 may have a cut-out portion on a base. The elongate slot allows the blade 3 to pass through the slot to contact and or penetrate the tissue to perform an incision. The travel distance of the trigger 4 relative to the housing 2 in a horizontal direction is dependent on the type of incision required by the lancet 1 and may be 1.75 mm for activation of the lancet 1 and correspondingly the blade 3.

The blade 3 creates a cut as it moves toward the end of a cutting path defined by the cam element 39 on the housing 2. A blade penetration depth may be in a range from 0.85 mm to 1.00 mm relative to a surface of the region of the person for an incision. The blade penetration depth may be adjusted by moving the position of the locator 30 on the blade holder 25. As the resilient member 5 extends toward an unbiased state and pushes the second trigger arm 22 toward an interior wall of the housing 2, the flexible member 24 deforms as the cam elements 31 of the blade holder 25 slide toward an end of the cam edge 61 and move up the cam edge 65 of the cam 40 provided at a bottom or base of the interior of the housing 2 with the cam elements 46 in contact with the cam edge 62 of the cam 39. The elastic deformation of the flexible member 24 generates elastic energy in the flexible member 24. As a result of the generated elastic energy in the flexible member 24, the second trigger arm 22 snaps toward the interior wall of the housing 2 once the cam elements 31, 46 are not engaging the cam 39, with the flexible member 24 pulling the blade 3 and the blade holder 25 toward and into a second stowed position as shown in FIG. 5. The cam edge 65 may be in an inclined plane relative to the base of the housing 2 and configured to urge the blade 3 and the blade holder 25 toward the second stowed position.

The second stop surface 35 and the inner wall of the housing 2 may form a gap 68 for holding a trigger arm tip 64 of the second trigger arm 22 to capture the trigger arm tip 64 and to prevent backward rotation of the trigger 4.

It will be appreciated that the resilient member 5 may be configured to include various designs configured to provide a push force on the second trigger arm 22 upon movement of the trigger 4. For example, the resilient member 5 may be designed as a torsion spring, a compression spring, a leaf spring, a cantilever spring, an extension spring or the like. The resilient member 5 may be made of a material such as, for example, a resilient steel material or any resilient material with creep resistant properties. Energy can be stored in a resilient member 5, whereby the resilient member is configured to exert a push force on the second trigger arm 22. The resilient member 5 may be made of a material with resiliency, high modulus of elasticity and strength, fatigue and creep resistance. Still further, the resilient member 5 may include one of: a helical torsion spring, a leaf spring, a cantilever spring or a helical compression spring. Although this is not illustrated, a skilled person will appreciate that the resilient member 5 may be configured to be a cantilever spring having one end integral with the second trigger arm 22 and a second end for engaging the first trigger arm 21.

The resilient member 5 may be made of a resilient metal such as, for example, high carbon steel, stainless steel, alloy steel or nickel-base alloy.

In an embodiment, the housing parts 7, 8 may incorporate a tongue and groove feature (not shown) around a periphery of the housing parts 7, 8 so as to ensure that users will not see between the housings if there is a gap between the housing parts 7, 8 when the housing parts are not fully mated.

Figure 6:
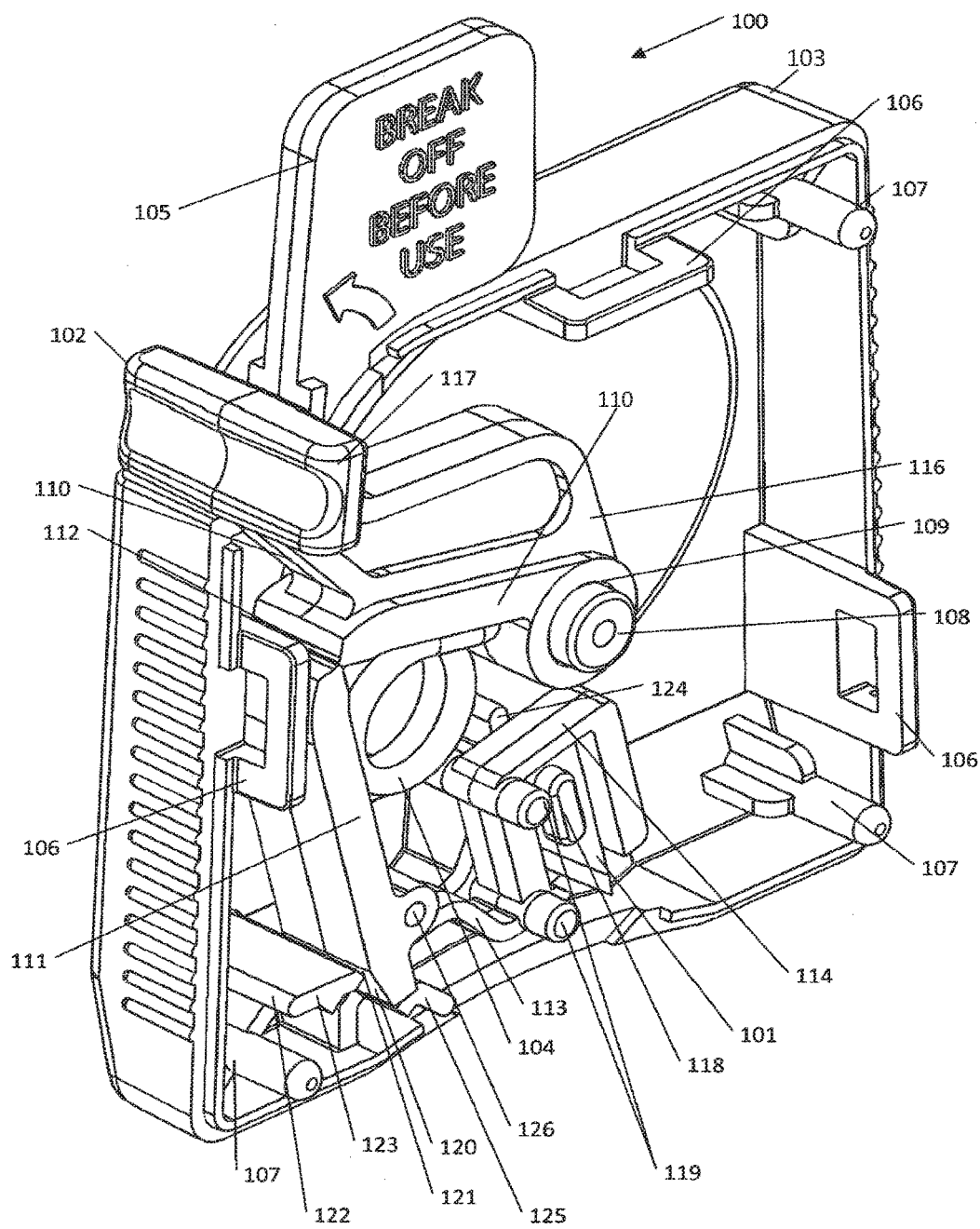
FIG. 6 is an orthogonal view of a lancet in a first stowed position.
Figure 7:
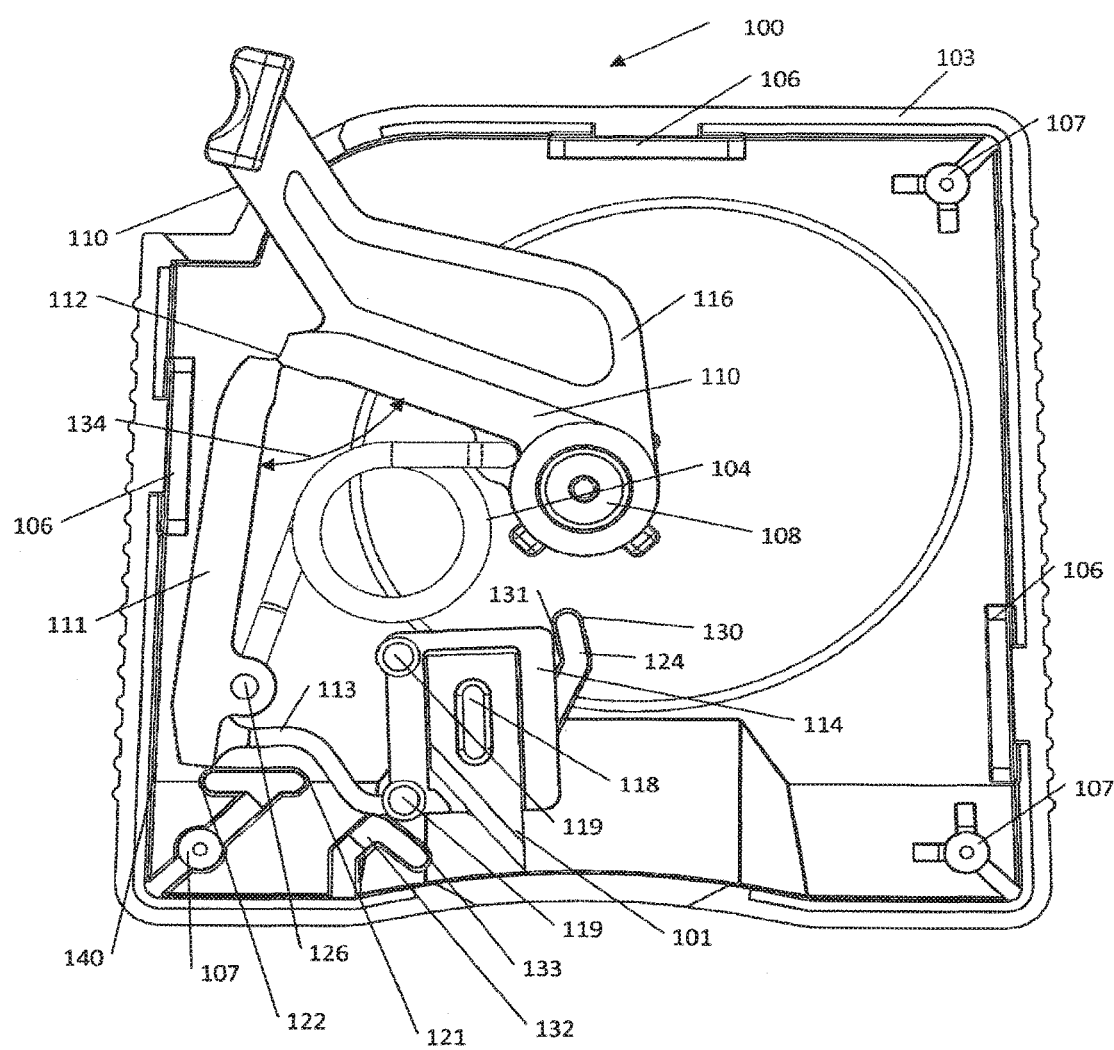
FIG. 7 is a front view of the lancet of FIG. 6 in a second stowed position.

In an embodiment, the resilient member may be a helical torsion spring as shown in FIG. 6. FIG. 6 is an orthogonal view of a partial assembly of a lancet 100 with a first housing part removed in a first stowed position. In the first stowed position, the lancet 100 is in a pre-cutting state. The housing of the lancet 100 has a second housing part 103 similar in configuration to the second housing part 6 of the lancet 1 in FIG. 1 and having substantially the same features including locating posts 107, interlocking snap features 106, a pivot 108, a rear member 123 having a first stopping surface 121 and a second stopping surface 122, a cam element 124 and a cam element 125. The lancet 100 also has a blade 101 and a trigger lock 105. In particular, the lancet 100 has a resilient member 104 configured to be a torsion spring. The lancet 100 has a trigger 102 having a first trigger arm 110 and a second trigger arm 111 configured for supporting the resilient member 104. A hole feature 109 may be defined in the trigger 102 for coupling the trigger 102 to the pivot 108. The second trigger arm 111 is connected to the first trigger arm 110 through a hinge 112, and a flexible member 113 is connected to the second trigger arm 111. The hinge 112 has a hinge angle 134 as shown in FIG. 7. The flexible member 113 functions in substantially the same way as the flexible member 24 of the lancet 1 and will not be elaborated further. The flexible member 113 may be connected to an end of the second trigger arm 111. Similar to the lancet 1 in FIG. 1, the trigger 102 may include a blade holder 114 for holding the blade 101, wherein the blade holder 114 is connected to one end of the flexible member 113. The blade 101 may be attached to the blade holder 114 via a locator 118 on the blade holder 114. The resilient member 104 may be supported by the trigger 102 via apertures 126 located on the second trigger arm 111 and apertures (not shown) located on the first trigger arm 110. The trigger 102 may be arranged within the housing between the pivot 108 and the first stop surface 121 of the second housing part 103 for enabling the resilient member 104 to store potential energy in a pre-cutting state of the blade 101. For example, in the first stowed position, the second trigger arm 111 abut the first stop surface 121 such that the resilient member 104 is in torsion and act between the first trigger arm 110 and the second trigger arm 111 to store spring energy in the trigger 102 in the first stowed position whereby the blade 101 is within the housing.

The trigger lock 105 may be removed to initiate actuation of the lancet 100 to allow the blade to be manoeuvred in a cutting path from a first stowed position through a cutting position to a second stowed position as shown in FIG. 7. Referring to FIG. 7, upon a movement of the first trigger arm 110, the trigger 102 rotates about the pivot 108 causing the second trigger arm 111 to slide relative the first stop surface 121, the resilient member 104 exerts a push force on the second trigger arm 111 toward the interior of the housing. The trigger 102 via the second trigger arm 111 transfers the push force by virtue of the flexible member 113 connecting the blade 101 to the second trigger arm 111 for moving the blade 101 in a cutting path from the first stowed position (shown in FIG. 6) through a cutting position to a second stowed position as shown in FIG. 7 in which the blade 101 is within the housing. The second trigger arm 111 pivots about the hinge 112 and by virtue of the force exerted by the resilient member 104, the second trigger arm 11 is moved toward an interior wall of the housing in the second stowed position. A second stop surface 122 abuts the second trigger arm 111 so as to prevent the trigger 102 from rotating and thereby keeping the blade 101 within the housing.

Figure 8:
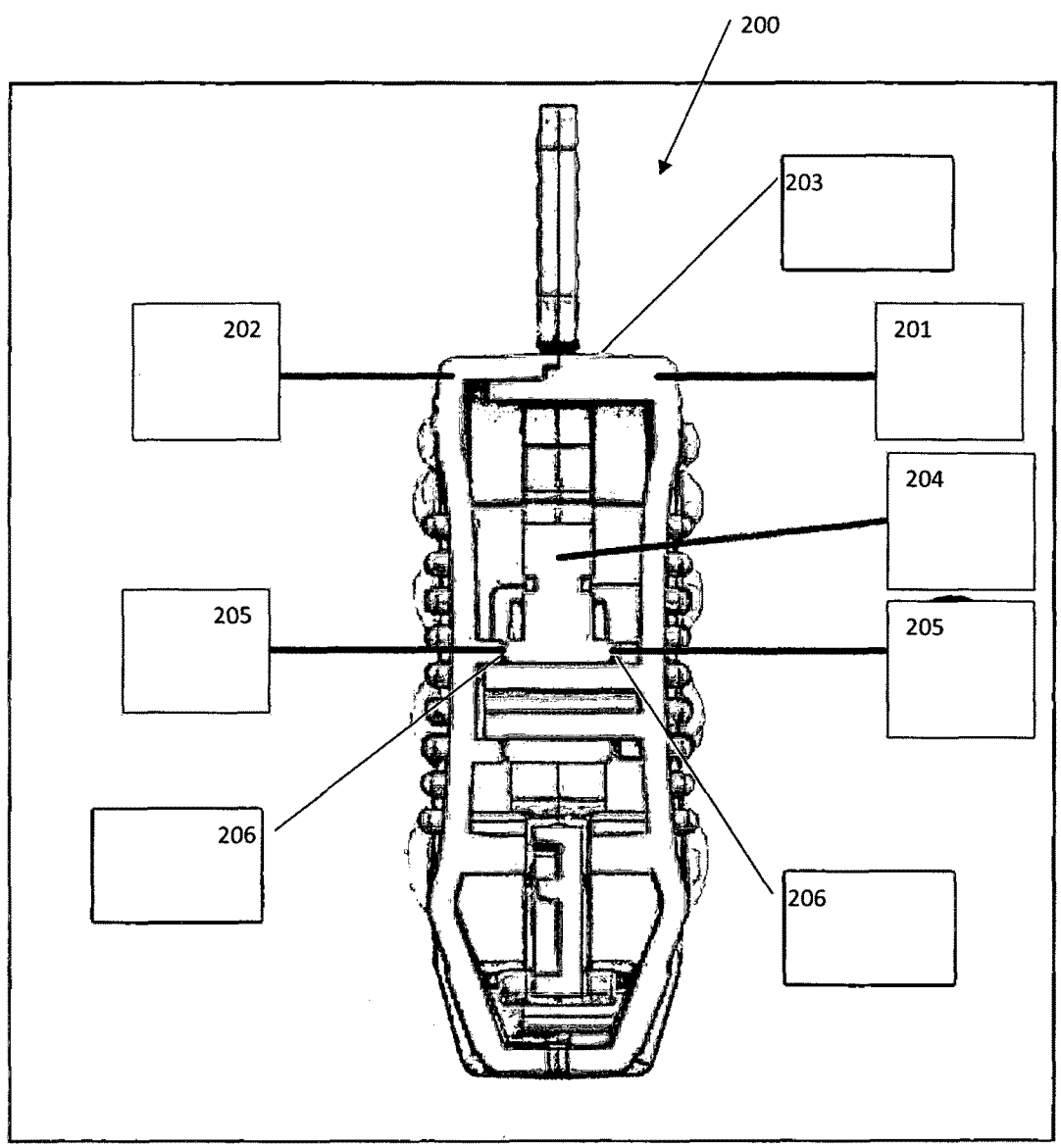
FIG. 8 is a section side view of a lancet.

FIG. 8 is a section side view of a lancet 200 according to an embodiment. The lancet 200 has substantially the same components as the lancet 1 of FIG. 1. The lancet 200 has a first housing part 201 and a second housing part 202, which cooperate upon assembly to form a housing 203 for housing a blade, a resilient member and a trigger 204. The trigger 204 is arranged between the first and second housing parts 201, 202 and may be made of a resilient material such as a plastic material. The plastic material may be such as, for example, a thermoplastic material or a polymer material. To minimize friction between the housing 203 and the trigger 204 during activation of the lancet 200, the trigger 204 may have a curved profile 205 at each side of the trigger 204 that interface with a flat surface 206 or flat surfaces 206 of the housing parts 201, 202. For example, the curved profile 205 may include radius features formed on outer edges of the trigger 204 for interfacing with flat surfaces 206 of the housing parts 201, 202.

Figure 9:
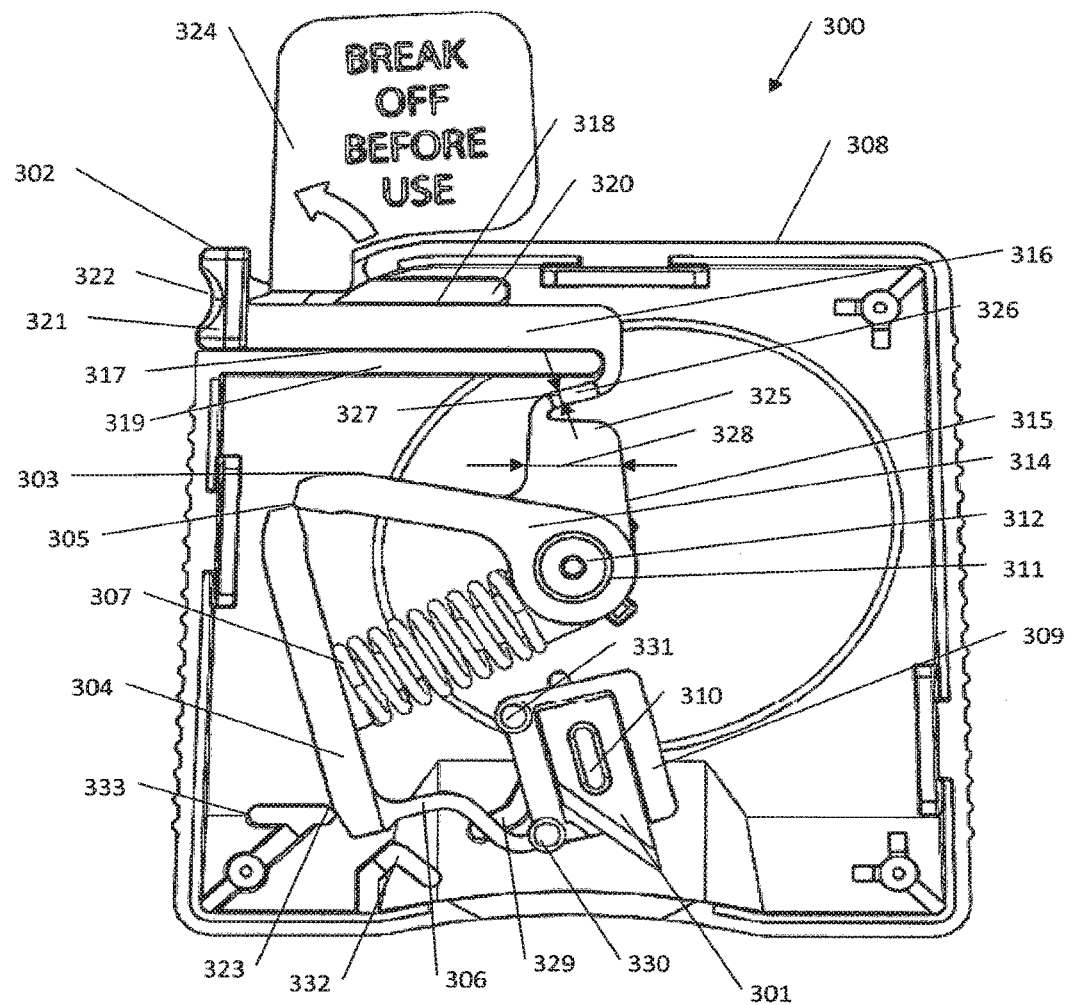
FIG. 9 is a front view of a lancet in a first stowed position.
Figure 10:
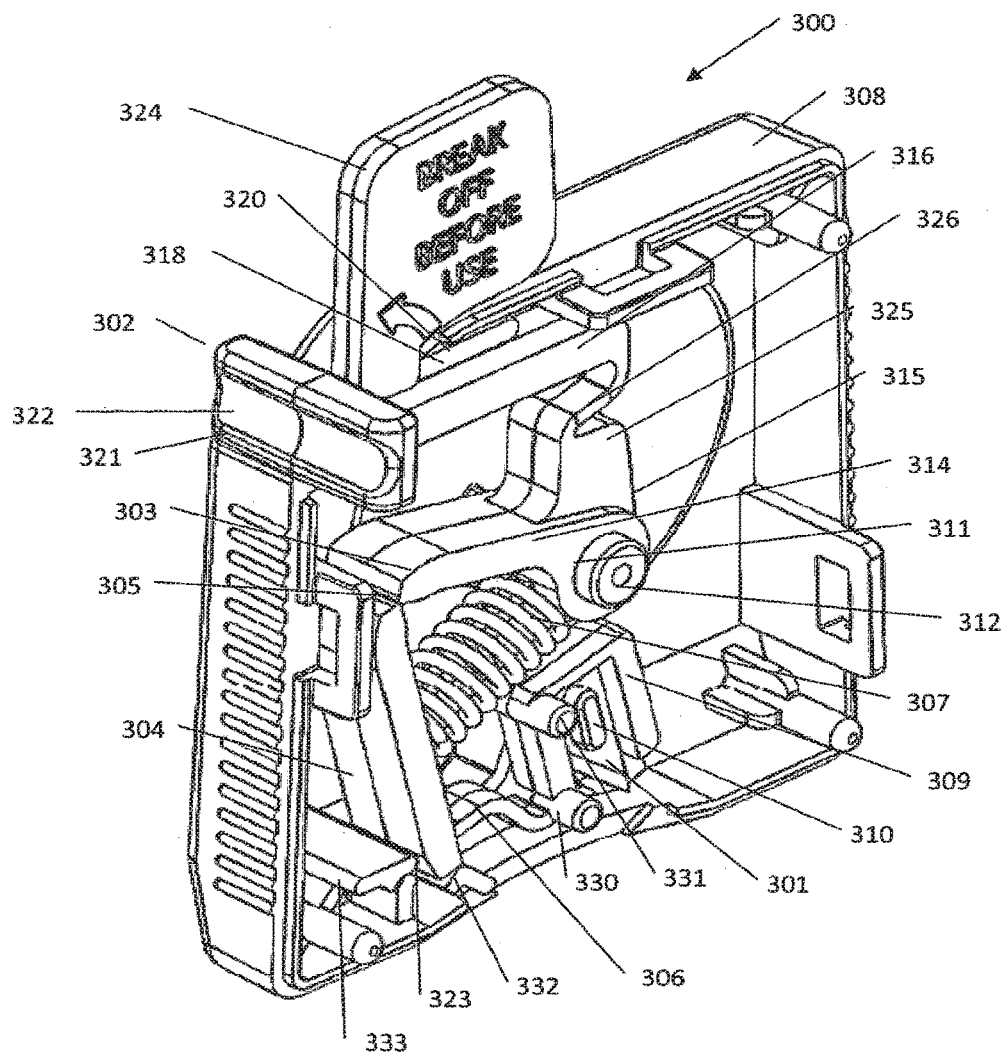
FIG. 10 is an orthogonal view of the lancet of FIG. 9.

FIG. 9 shows a front view of a lancet 300 for making an incision in a patient whereby the lancet 300 is in a first stowed position. FIG. 10 shows an orthogonal view of the lancet 300. The lancet 300 has a housing for housing a blade 301, and a trigger 302 comprising a first trigger arm 303, a second trigger arm 304 connected to the first trigger arm 303 through a hinge 305, and a flexible member 306 connected to the second trigger arm 304. A resilient member 307 is disposed within the housing in a pre-cutting state in which it stores energy and is arranged to exert a force for moving the second trigger arm 304 upon activation of the trigger 302. The housing has a first housing part and a second housing part 308. In FIGS. 9 and 10, the first housing part has been removed to illustrate a view of the arrangement of the blade 301, the trigger 302 and the resilient member 307 in the second housing part 308 in the first stowed position.

The flexible member 306 is configured to allow the blade 301 to be manoeuvred, upon actuation of the trigger 302, in a cutting path from the first stowed position through a cutting position to a second stowed position. Similar to the lancet 1 of FIG. 1, the trigger 302 may include a blade holder 309 connected to one end of the flexible member 306 for holding the blade 301, wherein the blade 301 may be attached to the blade holder 309 via a locator 310 on the blade holder 309.

The trigger 302 has a hole feature 311 defined in the trigger 302 for mounting the trigger 302 to a pivot 312 of the housing. The resilient member 307 may be arranged between the first trigger arm 303 and the second trigger arm 304 through supports or locators on the first and second trigger arms 303, 304. The hinge 305 is configured to allow the second trigger arm 304 to flex about the hinge 305 and move relative to the first trigger arm 303 to compress the resilient member 307 for assembly of the trigger 302 and the resilient member 307 in the housing.

Further, the first trigger arm 303 comprises a base portion 314 connected to the second trigger arm 304 through the hinge 305, a second portion 315 extending from the base portion 314 and a slider portion 316 connected to the second portion 315. The hole feature 310 may be defined in the base portion 314 of the first trigger arm 303. The slider portion 316 is configured for sliding along surfaces 317, 318 on the housing. The surface 317 may be provided on a support 319 located in the second housing part 308 and the surface 318 may be on a support 320 spaced apart from the support 319 to define a gap for receiving the third portion 316 of the first trigger arm 303. A handle portion 321 having a concave recess 322 may be connected to the slider portion 316 to increase grip and to give users a visual indication of where to place a finger tip for activating the lancet 300.

The trigger 302 and the resilient member 307 may be disposed in the second housing 308 by coupling the hole feature 310 to the pivot 311 and arranged such that the second trigger arm 304 abuts a first stopping surface 323 of the second housing part 308 to allow energy to be stored in the resilient member 307 in the pre-cutting state. A trigger lock 324 is connected to the trigger 302 and arranged within the housing for preventing movement of the trigger 302.

Upon removal of the trigger lock 324, the first trigger arm 303 may be moved by sliding the slider portion 316 along the surfaces 317, 318 on the housing. The second portion 315 has a support section 325 and a flexible section 326 connected to the slider portion 316. The second portion 315 is configured to be partially flexible to enable rotation of the trigger 302 upon movement of the trigger 302 through the slider portion 316. For example, the flexible section 326 has a cross-sectional thickness 327 substantially smaller relative to a cross-sectional thickness 328 of the support section 325 to allow the flexible section 326 to flex relative to the support section 325 upon movement of the slider portion 316. The sliding movement of the slider portion 316 causes the flexible section 324 to flex and rotate the trigger 302. As a result, the second trigger arm 304 slides relative to the first stop surface 323 and impart the force generated by the resilient member 307 to move with the blade 301 from a first stowed position through a cutting position and to a second stowed position. It will be appreciated that in the cutting position, the flexible member 306 is configured to manoeuvre the blade 301 to extend through an opening in the housing to slice skin of a patient to make an incision.

Similar to the blade holder 25 of FIG. 3, the blade holder 309 may be configured for cooperating with a cam element 329 located on the second housing part 308. For example, the blade holder 309 may also have cam followers 330, 331 for cooperating with the cam element 329 for guiding the blade holder 309 and the blade 301 through a path designed to define a cutting path for performing the incision. For example, the path may be designed to define a substantially parabolic cutting path for performing the incision.

Still further, the housing may include a cam 332 configured for guiding the blade holder 309 and the blade 301 toward the second stowed position within the housing. The housing may be configured to support the trigger 302 by including a second stop surface 333 for abutting the second trigger arm 312 to keep the second trigger arm 312 with the blade 301 within the housing in the second stowed position.

In all the embodiments, the cam elements located in the housing may be configured to cooperate with the blade to enable the blade to slice the skin of a patient to make an incision in a region such as, for example, in a heel.

In all the embodiments, the trigger may be a single unitary element consisting of a first trigger arm, a second trigger arm hinged to the first trigger arm, and a flexible member. Still further, a blade holder for holding a blade may be incorporated in the trigger to form the unitary element. Still further, a blade holder having cam elements, such as cam followers for cooperating with the housing to guide the blade in the cutting path may be incorporated in the trigger to form the unitary element. As lancets are generally used for taking blood samples and hence are used only once and disposed, an advantage of the trigger being a unitary element or having the blade holder and cam elements integral with the first and second trigger arms with the flexible member is to minimize material, manufacturing and assembly costs.

Further, the resilient member may be insert molded into the trigger. Still further, the first trigger arm and the second trigger arm may be molded as separate pieces and assembled together using the resilient member.

An advantage of the invention is to enable direct activation of the lancet with a consistent force to move the blade, which is independent of the user strength and ability.

While embodiments and applications of the present invention have been shown and described, it would be appreciated by a person skilled in the art that other modifications are possible without departing from the inventive concepts herein.

The invention claimed is:

1. A lancet comprising:
   a housing;
   a blade located in the housing;
   a trigger comprising a first trigger arm, a second trigger arm connected to the first trigger arm through a hinge;
   a flexible member connected to the blade, and to the second trigger arm at a location remote from the hinge, the flexible member configured to allow the blade to be maneuvered, upon activation of the trigger, in a nonlinear path from a first stowed position through a cutting position to a second stowed position; and
   a resilient member disposed within the housing between portions of the first trigger arm and the second trigger arm remote from the hinge in a pre-cutting state in which energy is stored, the resilient member arranged to exert a force for moving a portion of the second trigger arm remote from the hinge away from the first trigger arm upon activation of the trigger to pull the blade in the nonlinear path.

2. The lancet as claimed in claim 1, wherein the resilient member is secured to the first trigger arm and the second trigger arm.

3. The lancet as claimed in claim 1, wherein the flexible member is connected to an end of the second trigger arm.

4. The lancet as claimed in claim 1, wherein the housing comprises:
   a first stop surface for abutting the second trigger arm with the blade in the first stowed position; and
   a second stop surface for abutting the second trigger arm with the blade in the second stowed position, wherein the blade is within the housing in the first stowed position and the second stowed position.

5. The lancet as claimed in claim 4, wherein the second trigger arm is configured to slide relative to the first stop surface responsive to movement of the first trigger arm.

6. The lancet as claimed in claim 5, wherein the second trigger arm has a chamfered surface remote from the hinge.

7. The lancet as claimed in claim 4, wherein the housing includes a rear member having the first stop surface and the second stop surface, the rear member positioned to define a gap between the second stop surface and an inner wall of the housing for receiving the second trigger arm and the blade in the second stowed position.

8. The lancet as claimed in claim 7, further comprising a blade holder connected to the flexible member and holding the blade, the blade holder being configured to allow the blade to be maneuvered along the nonlinear path.

9. The lancet as claimed in claim 8, wherein the housing includes cam elements of a size and shape for guiding the blade through the nonlinear path in cooperation with cam elements of the blade holder.

10. The lancet as claimed in claim 9, wherein the cooperative cam elements of the housing and the blade holder are configured for guiding the blade through a parabolic path for performing an incision while in the cutting position.

11. The lancet as claimed in claim 9, wherein the housing includes an additional cam element located and configured for contacting the blade holder and guiding the blade while leaving the cutting position toward the second stowed position.

12. The lancet as claimed in claim 1, wherein the first trigger arm includes a base portion connected to the second trigger arm through the hinge, a second portion extending from the base portion, and a slider portion connected to the second portion, the second portion being configured, upon movement of the trigger, to allow the trigger to rotate about a pivot in the housing.

13. The lancet as claimed in claim 12, wherein the slider portion is configured to be slidable along surfaces in the housing.

14. The lancet as claimed in claim 1, wherein the resilient member is one of a helical torsion spring, a leaf spring, a cantilever spring or a helical compression spring.

15. The lancet as claimed in claim 14, wherein the resilient member is a cantilever spring integral with the trigger, the cantilever spring being configured to store energy in the precutting state.

16. The lancet as claimed in claim 1, wherein the resilient member is made of a resilient metal.

17. The lancet as claimed in claim 16, wherein the resilient member is made of one of high carbon steel, stainless steel, alloy steel and nickel-based alloy.

18. The lancet as claimed in claim 1, further comprising a trigger lock for preventing movement of the trigger.

19. The lancet as claimed in claim 1, wherein the flexible member has an S-shaped profile.

20. The lancet as claimed in claim 1, wherein the housing includes cam elements of a size and shape for guiding the blade through the nonlinear path.

* * * * *